United States Patent
Kraemer et al.

(10) Patent No.: US 7,856,286 B2
(45) Date of Patent: Dec. 21, 2010

(54) PROCESSING OF SHAPE DATA OF A DENTAL PROSTHESIS

(75) Inventors: Michael A. Kraemer, Landsberg am Lech (DE); Bernd K. Burger, Alling (DE); Holger Hauptmann, Sindelsdorf (DE); Guenter Hertlein, Seefeld (DE); Stefan Hoescheler, Munich (DE); Markus P. Salex, Martinsried (DE)

(73) Assignee: 3M Innovative Properties Company, Saint Paul, MN (US)

( * ) Notice: Subject to any disclaimer, the term of this patent is extended or adjusted under 35 U.S.C. 154(b) by 99 days.

(21) Appl. No.: 12/326,409

(22) Filed: Dec. 2, 2008

(65) Prior Publication Data

US 2009/0135182 A1 May 28, 2009

Related U.S. Application Data

(63) Continuation-in-part of application No. 10/550,992, filed as application No. PCT/EP2004/003169 on Mar. 25, 2004, now abandoned.

(30) Foreign Application Priority Data

Mar. 26, 2003 (DE) ................................. 103 13 690

(51) Int. Cl.
*G06F 19/00* (2006.01)
*A61C 13/08* (2006.01)
*G06G 7/48* (2006.01)

(52) U.S. Cl. .............................. 700/98; 433/205; 703/6

(58) Field of Classification Search .............. 433/201.1, 433/205, 223; 700/28, 29, 31, 97, 98, 118, 700/119; 703/1, 2, 6–11
See application file for complete search history.

(56) References Cited

U.S. PATENT DOCUMENTS

| 6,788,986 B1 * | 9/2004 | Traber et al. .................. 700/98 |
| 2002/0161563 A1 * | 10/2002 | Elabiad et al. .................. 703/8 |
| 2004/0158342 A1 * | 8/2004 | Wolf et al. ..................... 700/98 |

FOREIGN PATENT DOCUMENTS

| BE | 1011205 A3 | 6/1999 |
| JP | 09-019443 | 1/1997 |
| WO | WO 03007834 A1 * | 1/2003 |

OTHER PUBLICATIONS

Hansson, "A Fixed Partial Bridge in the Lower Jaw Supported by One Implant and One Tooth", A Biomechanical Analysis of the Effects of a Vertical Load on the Tooth, 1997, pp. 1-17.

* cited by examiner

*Primary Examiner*—Sean P Shechtman

(57) ABSTRACT

The invention relates to the processing of data regarding the three dimensional shape of a dental prosthesis, having two prosthesis sections and a connector section, wherein the connector section is connected to the two prosthesis sections and is less stable than the two prosthesis sections. The method includes the steps of (a) determining a stability parameter and a stability criterion for the connector section, (b) calculating the actual value for the stability parameter from the data, (c) checking the connector section to determine whether the actual value fulfills the stability criterion, and if not, generating a warning signal is to the user.

7 Claims, No Drawings

PROCESSING OF SHAPE DATA OF A DENTAL PROSTHESIS

CROSS-REFERENCE TO RELATED APPLICATIONS

This application is a continuation-in-part of pending prior U.S. patent application Ser. No. 10/550,992, which is a national stage filing under 35 U.S.C. 371 of PCT/EP2004/003169, filed Mar. 25, 2004, which claims priority to German Patent Application No. 103 13 690.8, filed Mar. 26, 2003, the disclosures of which are incorporated by reference in their entirety herein.

BACKGROUND OF THE INVENTION

It is known that the processing of data about the three-dimensional shape of a dental bridge coping may be accomplished by means of a CAD (computer-aided design) system which is part of a CIM (computer-integrated manufacturing) system. A variety of such systems are commercially available, including the LAVA system for the production of ceramic bridge copings, available from 3M ESPE AG, (Seefeld, Germany). With the LAVA system, the CAD component is connected to an optical scanner and to a NC-milling machine. The scanner captures the three-dimensional surface of a dentition impression and passes on the captured data to the CAD system. With the CAD system, the user can modify these surface data as desired, so as to draw up the three-dimensional shape of the bridge coping, and then send the corresponding shape data to the NC-milling machine. Finally, the NC-milling machine processes a zirconium oxide or zirconia ceramic blank into a desired article in accordance with the shape data.

After the milling of a zirconium blank with the LAVA system, the dental technician will typically provide the finished, milled bridge coping with a veneer in order to give the bridge the desired natural appearance. Typically, it is desirable for the connector section adjoining two neighboring bridge units to be as thin as possible, because it can interfere with the technician during the application of the veneer in the contact region between two neighboring bridge units. This is especially important for the anterior teeth, as these are considerably thinner than the posterior teeth and there is thus less space available for the veneer. However, the user must take care not to design the connector too thin or else it could create stability problems. The connector generally should be sufficiently stable to withstand the strong loadings that occur during the milling process, and also later when the patient who receives the bridge is chewing. It typically requires a great deal of experience for the dental technician to know how to achieve the right thickness of the connector to balance these various considerations. However, many dental technicians are lacking the necessary experience and costly training is often needed for them to acquire these skills.

SUMMARY OF THE INVENTION

The present invention relates to the production of a dental replacement, more specifically to the processing of data about the three-dimensional shape of a dental prosthesis having two prosthesis sections and a connector section, wherein the connector section is connected to the two prosthesis sections and is less stable than the two prosthesis sections.

As used herein, the term "dental prosthesis" is to be understood the broadest sense and is intended to include all types of dental replacements such as, for example, bridges, implants, and other dental prostheses, and parts of such dental prostheses such as, for example, bridge substructures or copings onto which a veneering is applied in order to obtain the finished bridge.

The quantity indications used herein, such as, for example, "two prosthesis sections" or "a connector section", are in general to be understood as a minimum value with the meaning of "at least two" or "at least one", etc., unless the limitation is expressed by wording such as "exactly" or "consists of".

The present invention thus includes, for example, not only two-unit bridge copings where the two units are connected by one connector, but also three- and multi-unit bridge copings, where each of the two neighboring units are connected by one connector. The units may be, as needed, anchors, intermediate units (also called pontics), or cantilever units. An anchor is fastened like a crown onto a tooth stump and serves as a bridge abutment. An intermediate unit or pontic is fastened between two units and not to a bridge abutment. A cantilever unit is fastened only to one unit and not to a bridge abutment.

With a one-piece bridge, i.e., a bridge which consists of one single piece and has no coping, neighboring bridge units border directly against one another, without a connector lying in between them. In this case, the transition area from one unit to the other is the connector section of the present invention, said transition area having a more or less prominent restriction or flattening due to the shape of the units, which are supposed to resemble to the natural appearance of the missing teeth.

DETAILED DESCRIPTION

The present invention provides a method for the processing of data regarding the three-dimensional shape of a dental prosthesis, having two prosthesis sections and a connector section, said connector section being connected to the two prosthesis sections and less stable than the two prosthesis sections. The method includes the steps of: (a) determining a stability parameter and a stability criterion for the connector section; (b) calculating a value for the stability parameter from the data; and (c) checking the connector section to determine whether the actual value fulfills the stability criterion, and if not, generating a warning signal, wherein the determination of the stability criterion is dependent on at least one of the following prosthesis attributes:

the configuration of the prosthesis; and/or
the position of the prosthesis inside the mouth; and/or
the material and/or the cross-sectional profile of the connector section; and/or
the type of the prosthesis sections adjoining the connector section.

The present invention is described in the following passages using an example of a bridge coping made of a zirconia ceramic material; however this example is not meant to be limiting of the invention, and the invention is not intended to be restricted to this one particular type of prosthesis.

The determination of the stability parameters and stability criteria for the connector section may be done by the user. For example, with the user may configure a three-unit bridge coping for the posterior teeth so that it has two anchors, one pontic, and two connectors in the form of circular cylinders. The user may further establish the requirement that the two connectors should have a circular cross-sectional area that meets a minimum specified threshold, e.g. a cross-sectional area of at least 9 $mm^2$, in order to achieve the desired stability. In this situation the stability parameter would be the "circular cross-sectional area" and the stability criterion would the requirement of a "circular cross-sectional area of at least 9 mm$^2$". The determination of stability parameters and stability criteria may alternatively be simplified for the user by allowing him to select a desired bridge coping from a product catalog or other library of options and then have the CAD system automatically generate a proposal for the stability parameters and stability criteria.

The above-described three-unit bridge coping provides an example of a "dental prosthesis," according to the invention. The anchors and pontic of the bridge coping are examples of "prosthesis sections." Its connectors are examples of "connector sections" as those terms are used herein. Accordingly, in this context, the phase "configuration of the prosthesis" refers to the number and arrangement of the constituent parts of the prosthesis, i.e. whether it is a two- or three-unit, single or two-span bridge coping with or without cantilever unit. In analyzing the stability of a bridge coping having multiple connections, it is usually sufficient to just consider the connector that experiences the greatest loading. For example, with a four-unit, single-span bridge without cantilever unit, two pontics are connected to one another and to the two anchors lying on the outer ends, by way of three connectors, so that the central connector lying between the two pontics is exposed to the largest loading. It is thus most often sufficient to monitor the stability of the central connector.

The profile of the cross-section of a connector may also deviate from the circular shape, and with a bridge coping for anterior teeth, for example, it may be stretched upwards and/or downwards, i.e. flattened in the front and/or back. Such a profile generally offers a better resistance against loadings from above and below than a circular profile of equal size.

The computation of the actual values of the cross-sectional areas from the shape data of the current bridge coping may be done, for example, automatically by means of a computer which displays the result on a screen. The subsequent verification that the actual value of the stability parameter is within the desired criteria (e.g. larger or equal to 9 mm$^2$), may also be done automatically, for example, by means of the computer, which displays the results on the screen. As the warning signal, a symbol may be shown on the screen, which is, for example, a red rectangle on a menu bar. Also, it is possible for a connector that is outside of the desired parameters (e.g. with a cross-section smaller than 9 mm$^2$) to be displayed on the screen in a different color.

In some implantations of the invention, the stability criterion may include a limit with which the actual value is compared. The limit may be an upper limit or a lower limit, or a limiting range defined by two outer limits (i.e., both an upper limit and a lower limit).

For example, the minimal cross-sectional area of the connector section may be one stability parameter and the stability criterion comprises a lower limit for it. For a connector in the form of a cylinder, the cross-sectional area is naturally constant over its length, however, for a connector with varying cross-sectional areas of the same profile, the specific location where the cross-sectional area is the lowest is where in will be the least stable and is used to define the minimum stability criterion.

In other implantations of the invention, the length of the connector section may be one stability parameter and the stability criterion comprises an upper limit for it. Due to the irregular shape of the units, the length of the connector is dependent on its location and orientation with respect to the units. Further, the stability of the connector generally decreases with increasing length.

It may be provided that the minimal sectional modulus of the connector section is one stability parameter and the stability criterion comprises a lower limit for it. The explanations previously made with respect to the cross-sectional area can analogously be applied to the sectional modulus.

It is also possible that the stability parameter is determined by means of the finite elements method and/or the boundary element method. These methods are best carried out by means of a computer and achieve a very exact determination of the stability even for complex structures.

It may further be provided that the calculation of the actual value conforms to a given specification. This specification may, for example, be provided by the user entering into the computer a control command for starting the calculation.

In another embodiment, the calculation of the actual value may be started according to a given time plan. The time plan may, for example, provide for a specific cycle or pulse according to which the calculation is started.

In yet another embodiment, the shape data can be changed or modified and the calculation of the actual value is started as soon as the data is changed or modified. The change or modification of the data can be made, e.g., by the user by means of a CAD system, but it is also possible that the CAD system automatically verifies the stability, using the current shape data, and in the case of a negative verification result modifies the data so that the stability is increased.

It may be provided that the warning signal notifies the user that the change or modification of the shape data has lead to the non-fulfillment of the stability criterion, and/or that such non-fulfillment has been is reversed or corrected.

It may be provided that the process is performed by means of a computer program. This program runs, for example, in a CAD system.

In a another aspect, the present invention relates to a data processing device for performing the process described above. The device includes:

an input device for the data;
a central unit connected to the input device, in which a program runs for the processing of the data according to the process; and
an output device for the warning signal, connected to the central unit.

This device may thus be a CAD system. The input device may, for example, be connected to the output of a scanner for the three-dimensional scanning of the surface of a dentition impression. The output device may, for example, be connected to the input of an NC-milling machine or other machine for the computer-supported processing of blanks.

It may be provided that an input device for changing or modifying the data and an output device for displaying the data are connected to the central unit. This input device may, for example, be a keyboard or a mouse. The output device may, for example, be a screen.

In yet another aspect, the present invention relates to a computer program which is adapted to perform the process according to the present invention.

In another aspect, the present invention relates to a computer program which, when it is run in a computer, performs the process according to the present invention.

In another aspect, the present invention relates to a computer program comprising commands that perform the process according to the present invention.

In another aspect, the present invention relates to a computer program which implements the process according to the present invention.

In another aspect, the present invention relates to a data carrier on which a computer program according to the present invention is stored. The data carrier may be, e.g., a floppy disc, a magnetic tape, a CD, a DVD, a memory stick, a hard disc, a RAM, or a ROM.

The present invention has now been described with reference to several embodiments thereof. It will be apparent to those skilled in the art that many changes can be made in the embodiments described without departing from the scope of the present invention. Thus the scope of the present invention should not be limited to the structures described in this application, but only by structures described by the language of the claims and the equivalents of those structures.

What is claimed is:

1. A method for the processing of data regarding a three-dimensional shape of a dental prosthesis having at least two prosthesis sections and at least one connector section, said connector section being connected to at least two prosthesis sections, the method comprising the steps of:
   (a) determining a stability parameter and a stability criterion for the connector section;
   (b) calculating a value for the stability parameter from the data in response to a user entering a change in the data; and
   (c) checking the connector section to determine whether the calculated value fulfills the stability criterion, and if not, then performing the steps of: generating a warning signal, modifying the data to change the value of the stability parameter in order to increase a stability of the connector section, and notifying the user of the modified data;

wherein the determination of the stability criterion is dependent on at least one prosthesis attribute selected from the group consisting of: a configuration of the prosthesis, a position of the prosthesis inside the mouth; a cross-sectional profile of the connector section; and the type of the prosthesis sections adjoining the connector section.

2. The method according to claim 1, wherein the stability criterion includes a limit to which the calculated value is compared.

3. The method according to claim 1, wherein a cross-sectional area of the connector section is one stability parameter and the stability criterion comprises a lower limit for the cross-sectional area of the connector section.

4. The method according to claim 1, wherein a length of the connector section is one stability parameter and the stability criterion comprises an upper limit for the length of the connector section.

5. The method according to claim 1, wherein a section modulus of the connector section is one stability parameter and the stability criterion comprises a lower limit for the section modulus of the connector section.

6. The method according to claim 1, wherein the modifying step comprises modifying the data based upon user input.

7. The method according to claim 1, wherein the modifying step comprises automatically modifying the data.

* * * * *